United States Patent
Gehles et al.

(10) Patent No.: US 9,852,955 B2
(45) Date of Patent: Dec. 26, 2017

(54) METHOD AND ARRANGEMENT FOR ANALYZING A SEMICONDUCTOR ELEMENT AND METHOD FOR MANUFACTURING A SEMICONDUCTOR COMPONENT

(71) Applicant: ams AG, Unterpremstaetten (AT)

(72) Inventors: Helene Gehles, Fuerth (DE); Thomas Bodner, Seiersberg (AT); Joerg Siegert, Graz (AT)

(73) Assignee: AMS AG, Unterpremstaetten (AT)

(*) Notice: Subject to any disclaimer, the term of this patent is extended or adjusted under 35 U.S.C. 154(b) by 0 days.

(21) Appl. No.: 15/343,117

(22) Filed: Nov. 3, 2016

(65) Prior Publication Data
US 2017/0133281 A1    May 11, 2017

(30) Foreign Application Priority Data

Nov. 11, 2015    (EP) .................................... 15194108

(51) Int. Cl.
*H01L 21/00* (2006.01)
*H01L 21/66* (2006.01)
(Continued)

(52) U.S. Cl.
CPC ........... *H01L 22/12* (2013.01); *G01N 21/643* (2013.01); *G01N 21/6458* (2013.01); *G02B 21/00* (2013.01); *G02B 21/0076* (2013.01); *H01L 21/02057* (2013.01); *H01L 21/3065* (2013.01); *H01L 22/10* (2013.01); *G01N 21/91* (2013.01); *G01N 21/94* (2013.01); *G01N 2021/646* (2013.01); *G01N 2021/8864* (2013.01); *G01N 2021/8877* (2013.01)

(58) Field of Classification Search
None
See application file for complete search history.

(56) References Cited

U.S. PATENT DOCUMENTS 6,256,094 B1    7/2001  Eyolfson et al.
6,338,822 B1 *  1/2002  Waldner ............... G01N 31/223
                                                        252/501.1
(Continued)

FOREIGN PATENT DOCUMENTS

JP           H02168148 A       6/1990

OTHER PUBLICATIONS

Gerasimova, V. I., et al., "Modification of the Optical Properties of Fluoropolymers by Supercritical Fluid Impregnation with Europium β-Diketonates", Russian Journal of Physical Chemistry B, vol. 4; No. 7, 2010, pp. 1149-1157.

(Continued)

*Primary Examiner* — Angel Roman
(74) *Attorney, Agent, or Firm* — McDermott Will & Emery LLP (57) ABSTRACT

According to the improved concept, a method for analyzing a semiconductor element comprising polymer residues located on a surface of the semiconductor element is provided. The method comprises marking at least a fraction of the residues by exposing the semiconductor element to a fluorescent substance and detecting the marked residues by visualizing the marked residues on the surface of the semiconductor element using fluorescence microscopy.

21 Claims, 2 Drawing Sheets

(51) Int. Cl.
  *G02B 21/00*    (2006.01)
  *H01L 21/02*    (2006.01)
  *H01L 21/3065*  (2006.01)
  *G01N 21/64*    (2006.01)
  *G01N 21/91*    (2006.01)
  *G01N 21/94*    (2006.01)
  *G01N 21/88*    (2006.01)

(56) References Cited

U.S. PATENT DOCUMENTS 8,357,536 B2     1/2013  Wuister
2007/0012337 A1  1/2007  Hillman et al.

OTHER PUBLICATIONS

Alapati. R. et al., "TSV Metrology and Inspection Challenges", IEEE, 2009, 4 pgs.
Jing, X, et al., "Non-Destructive Testing of Through Silicon Vias by High-Resolution X-Ray/CT Techniques", IEEE 14th Electronics Packaging Technology Conference, 2012, pp. 533-536.
Kim, S. B., et al., "Characteristics of the Post-Etch Polymer Residues Formed at the Via Hole and Polymer Removal Using a Semi-Aqueous Stripper", Journal of the Korean Physical Society, vol. 49, No. 5, 2006, pp. 1991-1997.
Meziani, M. et al, "Supercritical Carbon Dioxide in Semiconductor Cleaning", Handbook of Semiconductor Manufacturing Technology, 2007, CRC Press., pp. 6.5-6.6.
Stoffels, W. W., et al., "Polymerization of Fluorocarbons in Reactive Ion Etching Plasmas", Department of Electronic Science and Engineering, American Vacuum Society, 1998, pp. 87-95.

\* cited by examiner

METHOD AND ARRANGEMENT FOR ANALYZING A SEMICONDUCTOR ELEMENT AND METHOD FOR MANUFACTURING A SEMICONDUCTOR COMPONENT

BACKGROUND OF THE INVENTION

The present disclosure relates to a method and an arrangement for analyzing a semiconductor element and to a method for manufacturing a semiconductor component.

Processes for manufacturing semiconductor components may utilize polymer materials. For example polymer layers, such as fluoropolymer layers, may be used as passivation layers for purposes of etch protection, in particular in deep reactive ion etching, DRIE, processes. Such processes may for example be used to generate surface structures like through-semiconductor-vias, TSVs, trenches, cavities or the like. Another example for polymer materials in the context of semiconductor manufacturing are photoresists used for example for lithographic structuring or surface processing. Furthermore, other processes, for example layer deposition or a layer structuring processes, may generate polymer residues. Although the polymer materials may be removed in principle, polymer residues may remain.

Fluoropolymer residue removal may for example be done by sequences including ashing and/or wet cleaning steps including for example amine stripping solutions. However, in particular with increasing aspect ratios of surface structures, not only does the removal of polymer residues become more difficult, but also the inspection and analysis thereof. However, polymer residues may cause poor adhesion of subsequently deposited layers, for example for TSV isolation, TSV metallization and/or back side metallization. The poor adhesion may cause a reduced device yield.

Existing approaches for polymer residue analysis may use scanning electron microscopy to inspect individual surface structures. These approaches are typically very time-consuming and costly and/or involve destructive inspection methods.

SUMMARY OF THE INVENTION

The present disclosure provides an improved concept for analysis of a semiconductor element with respect to polymer residues that is non-destructive and achieves an improved efficiency.

According to the improved concept, polymer residues on the surface of a semiconductor element are marked or labelled by attaching or affixing particles or molecules of a fluorescent substance to the polymer residues. The fluorescent substance may for example be a substance denoted as fluorophore or fluorescent dye. Then, fluorescence microscopy is used for inspecting the semiconductor element and analyzing for example an amount and/or a distribution of the residues.

According to the improved concept, a method for analyzing a semiconductor element comprising polymer residues located on a surface of the semiconductor element is provided. The method comprises marking at least a fraction of the residues by exposing the semiconductor element to a fluorescent substance and detecting the marked residues by visualizing the marked residues on the surface of the semiconductor element using fluorescence microscopy.

The semiconductor element is for example a semiconductor die or chip or a semiconductor wafer. The semiconductor element may for example be a semiconductor wafer at any stage of manufacturing a semiconductor wafer, a semiconductor component or a semiconductor die or chip. In particular, after application of the method according to the improved concept for analyzing the semiconductor element, further layers may be deposited on the wafer.

The term surface includes all areas and parts of the semiconductor element that are accessible from the outside of the semiconductor device, in particular to the fluorescent substance, in particular without traversing a layer or a substrate of the semiconductor element.

The surface of the semiconductor element may comprise a front surface and/or a back surface of the semiconductor element, for example a front surface and/or a back surface of a semiconductor wafer, but is not limited to the front or back surface. In particular, the surface of semiconductor element may comprise one or more surfaces of sidewalls and/or bottom sides of surface structures.

It is noted that the term surface structure describes structures accessible from or connected to a surface, in particular a front or a back surface, of the semiconductor element, for example the semiconductor wafer. Thus, the surface structures may include any three-dimensional structure forming an elevated or deepened region with respect to the front or back surface of the semiconductor element or wafer. In particular, the surface structures may include one or more TSVs, trenches or cavities.

It is further noted that the term through-semiconductor via describes the same structures that may commonly be denoted as through-silicon via but highlighting that the vias may pass through a semiconductor material including but not limited to silicon.

The surface of the semiconductor element may include one or more, at a time when the method according to the improved concept is applied, terminal surface layers of the semiconductor element, in particular surfaces of the surface layers, or one or more parts thereof.

According to some implementations of the method, the polymer residues comprise or consist of an amorphous or a semicrystalline polymer material.

The polymer residues may for example origin from a manufacturing process used for the manufacturing of the semiconductor element. For example, the residues or a part of the residues may origin from an incomplete removal of a polymer passivation layer used for deep reactive-ion etching, DRIE.

Alternatively or in addition, the residues or a part of the residues may result from an incomplete removal of a photoresist, a polymer masking layer or another polymer layer used for the manufacturing of the semiconductor element. The residues may then for example comprise or consist of residues of a photoresist, for example a phenol formaldehyde resin such as a novolac.

Alternatively or in addition, the residues or a part of the residues may origin from other processes used for manufacturing of the semiconductor element, such as layer deposition processes, for example chemical vapor deposition and/or physical vapor deposition processes. In particular, the residues may originate from oxide or metal deposition processes. The residues may for example be generated during such processes and either be not removed afterwards or removed only incompletely.

The passivation layer and/or the residues, may comprise a fluoropolymer, for example Octafluorocyclobutane, and/or an acrylic polymer.

According to some implementations of the method, the semiconductor element is, for the marking, exposed to the fluorescent substance until the fluorescent substance is affixed or attached to at least a fraction of the residues.

In particular, the polymer residues may exist as particles with a polymer matrix and the fluorescent substance, in particular molecules and/or particles of the fluorescent substance, may be brought to or inside the polymer matrix and/or may be embedded in the polymer matrix to attach and/or affix the fluorescent substance to the residues. In other words, the fluorescent substance may be impressed to the polymer residues and/or the polymer residues are impregnated with the fluorescent substance.

The fluorescent substance, which is for example denoted as fluorophore, re-emits electromagnetic radiation, that is the fluorescent substance emits fluorescent electromagnetic radiation, when excited via illumination. The fluorescent electromagnetic radiation has a lower energy and a longer wavelength than the electromagnetic radiation used for the illumination. This principle is utilized by the fluorescence microscopy. Consequently, the marked residues, in particular the residues with the affixed fluorescent substance, maybe visualized by employing fluorescence microscopy.

The visualized residues may then for example be counted, their density, in particular their local density may be determined, their distribution on the surface of the semiconductor element may be characterized, a wafer map of the residues may be generated and/or other statistical evaluation of the residues on the surface of the semiconductor element may be carried out.

In particular, the residues may be marked and visualized by employing the method according to the improved concept, even though they may not be detectable with conventional techniques such as conventional light microscopy or scanning electron microscopy, which may only allow for inspection of a front or back surface of the semiconductor element and/or require a destruction of the semiconductor element.

An analysis using a method according to the improved concept also increases efficiency and reduces time consumption of the analysis, since the whole semiconductor element may be analyzed with respect to the residues.

Moreover, the method according to the improved concept is a non-destructive method for analysis of polymer residues, which is an advantage per se, since a semiconductor element used of the analysis may then be used also afterwards. Thus, a device yield may be increased.

According to some implementations of the method, the exposing the semiconductor element to the fluorescent substance comprises exposing the semiconductor element to a mixture, the mixture containing the fluorescent substance and an additional substance.

According to some implementations, the fluorescent substance is homogeneously mixed, in particular macroscopically and/or microscopically homogeneously mixed with the additional substance. In some implementations, the fluorescent substance is distributed within the additional substance homogeneously on a molecular level. In some implementation, the additional substance is a solvent and the mixture is a solution of the fluorescent substance in the additional substance.

According to some implementations, the fluorescent substance is heterogeneously mixed or microscopically heterogeneously mixed with the additional substance. In some implementations, the mixture is a suspension or a colloidal suspension of the fluorescent substance and the additional substance.

According to some implementations, the mixture and/or the solvent is in its gaseous phase, in its vapor phase, in its liquid phase or in its supercritical phase when the semiconductor element is exposed to the mixture.

Therein, the mixture is in its supercritical phase when a pressure and a temperature of the mixture lie within a supercritical range of a pressure-temperature phase diagram corresponding to the mixture. The pressure and the temperature of the mixture lie within the supercritical range if the pressure of the mixture is greater than a critical pressure of the mixture and the temperature of the mixture is greater than a critical temperature of the mixture. The critical pressure and the critical temperature define a critical point, in particular a liquid-vapor critical point or a liquid-gas critical point, of the mixture. The same holds for the solvent analogously.

The term surface particularly includes all areas and parts of the semiconductor element that are accessible to the mixture from the outside of the semiconductor device.

The different phases or states of the mixture and/or the solvent which may be used for the exposure of the semiconductor element to the mixture may feature different or partially different advantages. For example, when used in the gaseous or vapor phase, the handling and/or the preparation of the mixture and/or the solvent may be less involved and/or less costly.

On the other hand in the supercritical phase, the solubility of the fluorescent substance in the solvent may be increased with respect to the other mentioned phases. Hence, a concentration of the fluorescent substance in the mixture may be increased and consequently a greater amount of the fluorescent substance may be affixed to the residues and/or the time of exposure of the semiconductor element to the mixture may be reduced to achieve the desired marking.

Furthermore, the surface tension of a critical fluid is reduced compared to a liquid and the surface tension of a supercritical fluid is even smaller. Thus, using the mixture and/or the solvent in its supercritical phase may have to advantage that very narrow or very tight surface structures may be accessible to the mixture. Therefore, also polymer residues located on surfaces of TSVs, trenches or cavities with very small physical dimensions and/or very large aspect ratios may be marked by exposing the semiconductor element to the mixture. In addition, a diffusion rate of carbon dioxide into the polymer matrix may be increased. Thus, an effectivity of the marking and consequently of the analysis of the polymer residues is for example increased.

Using the mixture and/or the solvent in its liquid phase, may represent a trade-off between the advantages of the gaseous phase and the advantages of the supercritical phase.

According to some implementations, the mixture comprises, as the additional substance, carbon dioxide.

In such implementations, the fluorescent substance is dispersed or dissolved in the carbon dioxide when the semiconductor element is exposed to the mixture.

The critical temperature of carbon dioxide is 304.13 K, which is 30.980 ° C., while the critical pressure of carbon dioxide is 7.375 MPa, which is 72.79 atm.

Advantages of using carbon dioxide as solvent for the fluorescent substances include that carbon dioxide, in particular supercritical carbon dioxide, is easily available, highly stable, has a low toxicity and a relatively low critical temperature.

According to some implementations of the method, the mixture contains the carbon dioxide in its gaseous or vapor phase, in its liquid phase and/or its supercritical phase, in particular when the semiconductor element is exposed to the mixture.

Regarding the advantages of using carbon dioxide in its different phases, it is referred to the explanations with respect to the mixture above. In particular, if the mixture is used in its liquid phase, it may be advantageous to adjust the temperature and the pressure close to the critical point to benefit from a reduced surface tension and/or increased solubility of the fluorescent substance. For example, the temperature of the mixture may be adjusted to lie in a range from 20° C. to 35° C., for example 25° C. to 30° C. For example, the pressure of the mixture may be adjusted to lie in a range from 60 bar 90 bar.

According to some implementations, the method further comprises placing the semiconductor element in a pressure chamber, in particular a high-pressure chamber, and supplying the mixture to the pressure chamber.

In particular, the mixture may for example be supplied to the pressure chamber when the mixture is in its liquid or gaseous phase.

According to some implementations, the method comprises supplying the carbon dioxide to a pressure chamber, in particular a high-pressure chamber, and supplying the fluorescent substance to the pressure chamber.

In particular, the carbon dioxide may for example be supplied to the pressure chamber when the carbon dioxide is in its solid, in its liquid or in its gaseous phase. The fluorescent substance may for example be supplied to the pressure chamber by supplying an additional mixture containing the fluorescent substance to the pressure chamber. The additional mixture may for example contain an additional solvent, for example dimethyl sulfoxide, an alcohol such as isopropyl alcohol or water, for example deionized water. The fluorescent substances for example dissolved in the additional solvent, when supplied to pressure chamber.

The method for example further comprises generating the mixture within the pressure chamber. That is, after being supplied with the additional mixture to the pressure chamber, the fluorescent substance is mixed with, for example dissolved in, the carbon dioxide to generate the mixture.

According to some implementations, the method comprises transferring the mixture to its liquid phase, in particular from its gaseous phase to its liquid phase.

According to some implementations, the method comprises transferring the mixture to its supercritical phase, in particular from its gaseous phase or from its liquid phase to its supercritical phase.

According to some implementations, the method further comprises, for the transferring, increasing a pressure and/or a temperature inside the pressure chamber.

If the mixture is supplied to the pressure chamber in its gaseous phase, it may for example be transferred to the liquid phase by increasing at least one of the pressure and the temperature inside the pressure chamber. Then, the mixture may be transferred to the supercritical phase by increasing at least one of the pressure and temperature inside the pressure chamber. Alternatively, the mixture may not be transferred to the critical or supercritical phase.

If the mixture is supplied to the pressure chamber in its liquid phase, it may be transferred to the supercritical phase by increasing at least one of the pressure and temperature inside the pressure chamber. Alternatively, the mixture may not be transferred to the supercritical phase.

Accordingly, the semiconductor element is exposed to the mixture in its supercritical phase if the mixture is transferred to its supercritical phase. Analogously, the semiconductor element is exposed to the mixture in its liquid phase if the mixture is not transferred to its supercritical phase.

According to some implementations, the method further comprises transferring the mixture or the carbon dioxide to its gaseous phase after the marking of the residues. To this end, for example the pressure and/or the temperature inside the pressure chamber is decreased.

In such implementations, the carbon dioxide may be easily pumped down after the marking. The fluorescent substance, however, remains affixed to the residues. That is the residues remain marked. Alternatively or in addition, the carbon dioxide may be released from the pressure chamber by opening the pressure chamber after the mixture order carbon dioxide has been transferred to the gaseous phase.

According to some implementations of the method, the visualizing of the marked residues using fluorescence microscopy comprises illuminating at least a part of the semiconductor element, in particular illuminating the surface on which the polymer residues are located, with electromagnetic radiation, in particular with electromagnetic radiation having a wavelength matching or approximately matching an absorption wavelength of the fluorescent substance. The method further comprises detecting fluorescent electromagnetic radiation being emitted by the affixed fluorescent substance as a response to the illumination.

For the fluorescence microscopy, a fluorescence microscope, in particular a confocal fluorescence microscope may be used. The fluorescence microscope comprises a light source, for example a laser. The laser may for example be implemented as a gas laser such as a helium-neon laser.

The fluorescence microscope may be implemented as a conventional fluorescence microscope. The fluorescence microscope may also be combined with the pressure chamber to a cluster tool.

The fluorescent substance has an absorption wavelength and an emission wavelength. The wavelength of the electromagnetic radiation used for the illumination matches or approximately matches the absorption wavelength of the fluorescent substance. The wavelength of the electromagnetic radiation used for the illumination is for example adjusted to the absorption wavelength of the fluorescent substance. Alternatively or in addition, the fluorescent substance may be selected such that its absorption wavelength matches or approximately matches the wavelength of the electromagnetic radiation used for the illumination or lies within a wavelength range of electromagnetic radiation achievable by the fluorescence microscope, in particular the light source.

Consequently, the fluorescent substance affixed to the residues being illuminated with the electromagnetic radiation is excited and consequently emits fluorescent electromagnetic radiation with a wavelength corresponding to the emission wavelength.

The emitted fluorescent electromagnetic radiation is detected for example by a photosensitive device, for example a camera, of the fluorescence microscope. The photosensitive device then may generate an image of the semiconductor element or of the illuminated part of the semiconductor element. In this image, the fluorescent substance affixed to the residues appears as a bright spot, while a non-fluorescent background, that is areas of the illuminated part of the semiconductor element containing no polymer residues with the fluorescent substance affixed, appears dark. In this way, the marked residues are visualized and detected.

The illuminating of the at least a part of the semiconductor element and the subsequent detection of the fluorescent electromagnetic radiation may be repeated for different focus levels, for example focusing the illuminating electromagnetic radiation to different depths of a surface structure, for example a TSV, of the semiconductor element. Then, a three-dimensional fluorescence image of the illuminated part of the semiconductor element, for example of the surface structure, may be generated by merging the images corresponding to the different focus levels.

The fluorescent substance is for example selected with respect to its organic functionalities and its absorption wavelength. Therein, fluorescent substances with a higher absorption wavelength, for example greater than 600 nm, may have the advantage of a lower degree of fluorescence fading since the radiation used for illumination is then less energy rich. This may allow for longer inspection times and for example even repeated inspections with consistent fluorescence intensity.

In some implementations of the method, the fluorescent substance comprises an organic compound, for example an aromatic organic compound. The organic compound may for example comprise a fluorescent organic dye. Molecules comprised by the organic compound, the aromatic organic compound and/or the fluorescent organic dye may for example comprise one or more functional organic groups such as a carboxyl group.

The fluorescent substance may comprise for example a cationic fluorescent dye such as an ATTO 647N fluorescent dye being commercially available from ATTO-TEC GmbH as of this writing, an Alexa Fluor® fluorescent dye being commercially available from Thermo Fisher Scientific Inc. as of this writing and/or a cyanide fluorescent dye such as a Cy5 fluorescent dye, for example a Cy®5 fluorescent dye being commercially available from Thermo Fisher Scientific Inc. as of this writing.

The mentioned particular examples for fluorescent organic dyes feature absorption wavelengths and emission wavelengths in the red visible range or the near infrared range. That is, they may be particularly suitable for implementations of the method, wherein red visible light or infrared light is used for the fluorescence microscopy. However, depending on the electromagnetic radiation, in particular the wavelength of the electromagnetic radiation, being used for the fluorescence microscopy, obviously also other fluorescent organic dyes may be used that feature an absorption wavelength in the respective range. A number of suitable organic fluorescent dyes are commercially available as of this writing.

According to some implementations of the method, the semiconductor element comprises at least one surface structure and the residues located on the surface of the semiconductor element are located on a surface of the at least one surface structure.

According to some implementations of the method, the surface structure comprises at least one of the following: a through-semiconductor-via, TSV, a trench, a cavity.

The surface of the at least one surface structure where the residues are located on comprises for example a surface of a sidewall of the surface structure and/or of a bottom of the surface structure.

The surface structure, in particular the TSV, is for example generated employing a DRIE process, for example a Bosch process. The DRIE process comprises for example a series of alternating etch and deposition cycles. During a deposition cycle, an already generated part of the surface structure, in particular a sidewall and a bottom of the TSV, is coated with a passivation layer, in particular a polymer layer, for example a fluoropolymer layer. In a subsequent etch cycle, reactive radicals, for example assisted by incident ions, remove the polymer layer from the bottom of the surface structure and etch an underlying material, for example a substrate material of the semiconductor element. Since the etching is highly anisotropic, the polymer layer prevents the sidewall of the surface structure from lateral etching by the radicals.

After the etching of the surface structure is completed, a cleaning step is used to remove the remaining polymer layer. Since the removal of the polymer layer may be incomplete, the polymer residues may remain on the surface of the surface structure.

According to the improved concept also a method for manufacturing a semiconductor component is provided. The method comprises processing a surface of a semiconductor element, wherein a polymer material is utilized or generated. The method further comprises analyzing the semiconductor element comprising polymer residues originating from the polymer material by employing a method for analyzing a semiconductor element according to the improved concept.

According to some implementations of the method for manufacturing, the analyzing comprises marking at least a fraction of the residues by exposing the semiconductor element to a fluorescent substance and detecting the marked residues by visualizing the marked residues on the surface of the semiconductor using fluorescence microscopy.

According to some implementations, the method for manufacturing comprises depositing at least one further layer to the semiconductor element after the analyzing of the semiconductor element. The at least one further layer comprises for example an isolator layer, in particular a TSV spacer layer, or a metallization layer, in particular a TSV metallization layer and/or a back side metallization layer.

Is highlighted that any implementation of a method for analyzing a semiconductor element according to the improved concept may be used within a method for manufacturing a semiconductor component according to the improved concept.

According to some implementations of the method for manufacturing, the step of processing the surface of the semiconductor element comprises generating a surface structure, for example a TSV, a trench or a cavity, by employing a DRIE process. The DRIE process comprises depositing a polymer layer as a passivation layer for preventing from lateral etching. The polymer residues located on the surface of the semiconductor element origin or partially origin from the polymer layer, in particular from the polymer layer being incompletely removed.

According to some implementations of the method for manufacturing, the step of processing the surface of the semiconductor element comprises depositing a photoresist. The polymer residues located on the surface of the semiconductor element origin or partially origin from an incomplete removal of the photoresist.

According to some implementations of the method for manufacturing, the step of processing the surface of the semiconductor element comprises a layer deposition process or a layer structuring process. The polymer residues located on the surface of the semiconductor element are generated or partially generated during the layer deposition process for the layer structuring process.

According to the improved concept, also an arrangement for analyzing a semiconductor element comprising polymer residues located on a surface is provided. The arrangement comprises a pressure chamber configured to receive the semiconductor element, a mixing chamber configured to generate a mixture containing liquid carbon dioxide and a fluorescent substance within the mixing chamber and a feed line connecting the mixing chamber and the pressure chamber via an intake valve to supply the mixture to the pressure chamber. The arrangement further comprises a control unit configured to control a pressure and a temperature inside the pressure chamber and the intake valve to expose the semiconductor element to the mixture until the fluorescent substance is affixed to at least a fraction of the residues. The arrangement also comprises a fluorescence microscope configured to visualize the residues to which the fluorescent substance is affixed.

A method for analyzing a semiconductor element according to the improved concept may be carried out using an arrangement according to the improved concept.

According to some implementations of the arrangement, the pressure chamber and the fluorescence microscope are separated from each other. Such implementations, the semiconductor element is removed from the pressure chamber after the marking of at least the fraction of the residues. Then the semiconductor element is transferred to the fluorescence microscope for the detecting of the marked residues.

According to some implementations of the arrangement, the fluorescence microscope is configured to visualize the marked residues while the semiconductor element is located inside the pressure chamber.

In such implementations, the fluorescence microscope and the pressure chamber are combined within a single cluster tool. Such implementations have the advantage that the semiconductor element does not have to be transferred to another location between the marking of at least the fraction of the residues and the detecting of the marked residues.

According to some implementations of the arrangement, the fluorescence microscope is configured to illuminate at least a part of the semiconductor element with electromagnetic radiation and to detect fluorescent electromagnetic radiation being emitted by the affixed fluorescent substance as a response to the illumination. In this way, the fluorescence microscope may visualize the residues to which the fluorescent substance is affixed.

Further implementations of the arrangement are readily derived from the various implementations of the method for analyzing a semiconductor element and vice versa.

BRIEF DESCRIPTION OF THE DRAWINGS

In the following, the improved concept is explained in detail with the aid of exemplary implementations by reference to the drawings. Components that are functionally identical or have an identical effect may be denoted by identical references.

Identical components and/or components with identical effects may be described only with respect to the figure where they occur first and their description is not necessarily repeated in subsequent figures.

In the drawings.

DETAILED DESCRIPTION

Figure 1:
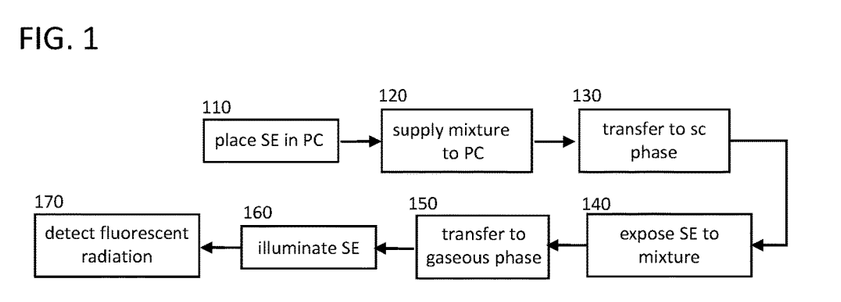
FIG. 1 shows a flow chart representing an exemplary implementation of a method for analyzing a semiconductor element according to the improved concept.

FIG. 1 shows a flow chart representing an exemplary implementation of a method for analyzing a semiconductor element according to the improved concept.

According to block 110, a semiconductor element SE comprising polymer residues located on a surface of the semiconductor element is placed in a pressure chamber PC. In block 120, a mixture containing a fluorescent substance is supplied to the pressure chamber PC. In addition to the fluorescent substance, in the mixture comprises for example a solvent, for example carbon dioxide, in particular liquid carbon dioxide. The fluorescent substance is for example dissolved in the solvent. The fluorescent substance is for example implemented as a fluorescent dye, in particular an organic fluorescent dye. The organic fluorescent dye comprises for example an aromatic organic compound.

As an alternative to supplying the mixture to the pressure chamber PC, the fluorescent substance and the carbon dioxide may be supplied to the pressure chamber PC separately. Then, the fluorescent substance is for example supplied to the pressure chamber PC in form of an additional mixture containing the fluorescent substance dissolved in additional solvent such as dimethyl sulfoxide, isopropyl alcohol or deionized water. The carbon dioxide may for example be supplied to the pressure chamber PC as gaseous, liquid or solid carbon dioxide. Then, the mixture, in particular the solution of the fluorescent substance in the carbon dioxide may be generated within the pressure chamber for example by evaporating the solid carbon dioxide.

In optional block 130, the mixture is transferred from its liquid phase to its supercritical phase or close to its supercritical phase for example by increasing the temperature in the pressure chamber PC beyond or close to the critical temperature of carbon dioxide and/or by increasing the pressure in the pressure chamber PC beyond or close to the critical pressure of carbon dioxide. For further details it is referred to FIG. 4 and the corresponding description.

According to block 140, the semiconductor element SE is exposed to the mixture and therefore to the fluorescent substance. In particular, the semiconductor element SE may be exposed to the mixture until the fluorescent substance is affixed to at least a fraction of the residues. Consequently, by exposing the semiconductor element SE to the mixture and the fluorescent substance, at least the fraction of residues, to which the fluorescent substance is affixed, is marked.

By exposing the semiconductor element SE to the mixture, the mixture and consequently the fluorescent substance is for example brought into the polymer matrix of the residues. It may be particularly advantageous to use carbon dioxide in its supercritical phase, since a solubility of the fluorescent substance in the carbon dioxide may be increased and a surface tension of the mixture may be decreased in this way. Alternatively, the carbon dioxide may be used in its liquid phase, for example at a temperature and pressure close to the critical point. Also in this way, a sufficiently high solubility of the fluorescent substance and sufficiently low surface tension may be achieved. Consequently an increased amount of the fluorescent substance may be brought into the polymer matrix. In a sense, the residues are impregnated with the mixture in this way.

When the semiconductor element is exposed to the mixture for affixing the fluorescent substance, a pressure inside the chamber is for example between 30° C. and 40° C., for example between 32° C. and 35° C. A pressure inside the chamber is then for example between 60 bar and 80 bar, for example between 60 bar and 70 bar.

According to block 150, the mixture or the carbon dioxide is transferred to its gaseous phase for example by decreasing the temperature and/or the pressure inside the pressure chamber PC. The fluorescent substance affixed to the residues, however, remains affixed to the residues. The gaseous carbon dioxide may then be pumped down.

In blocks 160 and 170, the marked residues are detected by visualizing the marked residues on the surface of the semiconductor using fluorescence microscopy. To this end, in block 160 at least a part of the semiconductor element is illuminated with electromagnetic radiation, for example with a fluorescence microscope, in particular a light source of the fluorescence microscope. In this way, the fluorescent substance affixed to at least the fraction of the residues is illuminated with the electromagnetic radiation and thus excited. The light source may for example be implemented as a laser, for example a helium-neon laser.

The electromagnetic radiation used for illuminating the semiconductor element may have a wavelength matching or approximately matching an absorption wavelength of the fluorescent substance. Hence, by illuminating the fluorescent substance is transferred to an excited state. As a consequence, the fluorescent substance emits fluorescent electromagnetic radiation as a response to the illumination. In block 170, the fluorescent electromagnetic radiation is detected for example with the fluorescence microscope, in particular with a photosensitive device, for example a camera, of the fluorescence microscope.

Based on the detected fluorescent radiation, for example images of the semiconductor element or of the marked residues may be generated. These images may for example be used to perform a statistical evaluation of the residues located the semiconductor element. In particular, a wafer map representing the residues may be generated based on the images.

Figure 2:
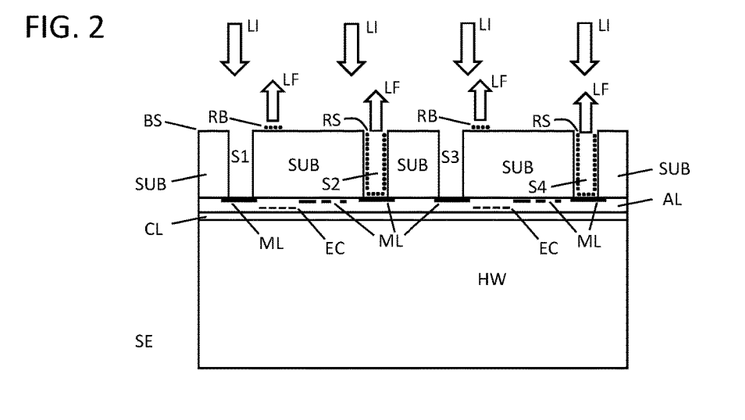
FIG. 2 shows a cross section of a semiconductor element and aspects of an exemplary implementation of a method for analyzing the semiconductor element according to the improved concept.

FIG. 2 shows a cross section of a semiconductor element and aspects of an exemplary implementation of a method for analyzing the semiconductor element according to the improved concept.

The semiconductor element is for example a semiconductor wafer, in particular a semiconductor wafer at a certain stage of manufacturing. In FIG. 2, only a part of the semiconductor wafer may be shown. The semiconductor wafer comprises a semiconductor substrate SUB and an active layer stack AL arranged on the substrate SUB. In the shown example, the semiconductor element SE further comprises an optional handling wafer HW and an optional connecting layer CL connecting the handling wafer HW and the active layer stack AL. Using the handling wafer HW may be advantageous the substrate SUB is relatively thin at the corresponding stage of manufacturing. This may origin for example from a preceding wafer thinning step.

The active layer stack AL comprises for example electronic components EC, which contains for example active circuitry such as transistor circuitry and/or CMOS circuitry. The active layer stack AL comprises for example metallization layers ML. The metallization layers ML may for example be electrically connected to at least some of the electronic components EC (connection not shown).

The substrate SUB comprises through-semiconductor-vias, TSVs, in particular four TSVs S1, S2, S3, S4. The TSVs S1, S2, S3, S4 are for example connected to the metallization layers ML. The TSVs S1, S2, S3, S4 are for example intended for providing an electrical connection of the metallization layers ML to a back side metallization (not shown) on a back side BS of the substrate SUB. Therein, the back side BS of the substrate SUB corresponds to a side of the substrate SUB being opposed to the side of the substrate SUB facing the active layer stack AL. The back side BS also represents a back side of the wafer at the shown stage of manufacturing. For providing the electrical connection, a TSV-metallization layer (not shown) may be deposited on the sidewalls and/or the bottom of the TSVs S1, S2, S3, S4. In addition, a spacer layer (not shown), in particular a dielectric spacer layer, may be arranged between the TSV-metallization layer and the material of the substrate SUB. The spacer layer may for example comprise or consist of silicon dioxide.

The semiconductor element SE further comprises for example polymer residues RB located on the back side BS and/or polymer residues RS located on a sidewall and/or a bottom of the second and the fourth TSVs S2, S4. It is highlighted that in FIG. 2 the specific locations of the polymer residues RB, RS are chosen exemplarily only. In particular, the semiconductor element SE may comprise polymer residues at additional and/or different positions, in particular on sidewalls and/or bottoms of the first and the third TSVs S1, S2.

The TSVs S1, S2, S3, S4 are for example generated employing a deep reactive-ion etching, DRIE, process comprising a series of alternating etch and deposition cycles. During the deposition cycles, a polymer layer is deposited as a passivation layer covering the sidewalls or parts of the sidewalls of the TSVs S1, S2, S3, S4 to prevent from lateral etching during the etch cycles. After finishing all of the etch cycles, the polymer layer may be removed for example by using a cleaning process including ashing and/or wet cleaning steps using for example amine stripping solutions.

However, the removal of the polymer layer may be incomplete giving rise to the residues RS located in the TSVs and/or the residues RB located on the back side BS of the substrate SUB.

In addition or alternatively, the polymer residues RS, RB may for example originate from an incomplete removal of a photoresist layer. The photoresist layer may for example be utilized for example for structuring further layer for example after generating the TSVs S1, S2, S3, S4. The further layer may for example be a metal layer, in particular the back side metallization and/or the TSV-metallization layer, or the spacer layer.

In addition or alternatively, the residues may for example originate from processes used for depositing the further layer.

The residues RS, RB may for example comprise fluoropolymer and/or acrylic polymer materials. The residues RS, RB may for example comprise polymer particles with a thickness in the order of a several nanometers.

The residues RS, RB may be disadvantageous for a further processing of the semiconductor element SE. In particular, the residues RS, RB may reduce an adhesion of additional layers to be deposited on the semiconductor element SE. Therefore, it is desirable to analyze the semiconductor element SE with respect to the amount, density, distribution or the like of the residues RS, RB.

To this end, the semiconductor element SE of FIG. 2 may be analyzed with a method for analyzing according to the improved concept, for example as described with respect to FIG. 1.

Thus, the residues RB, RS are marked by affixing the fluorescent substance to the residues RB, RS as described for example with respect to FIG. 1. Then the marked residues are detected using fluorescence microscopy as described for example with respect to FIG. 1.

FIG. 2 also shows incoming electromagnetic radiation LI which is for example generated by the fluorescence microscope for illuminating the semiconductor element SE. Furthermore, fluorescent electromagnetic radiation LF is shown that is being emitted by the fluorescent substance affixed to the residues RB, RS in response to the illumination as described for example with respect to FIG. 1. Images may be generated based on the detected electromagnetic radiation LF.

It is noted that, instead of the semiconductor wafer, the semiconductor element SE may for example be a semiconductor chip or die.

Figure 3:
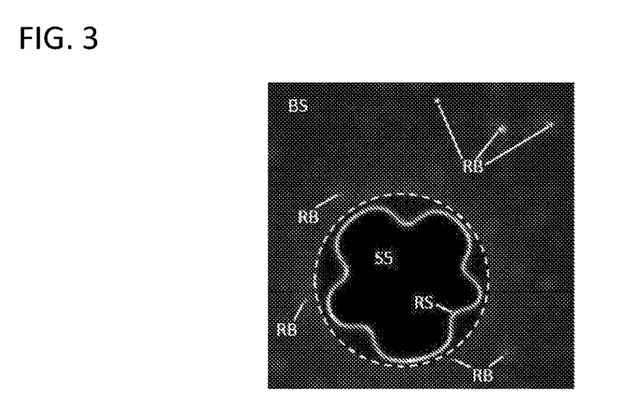
FIG. 3 shows an image of a top view of a semiconductor element analyzed employing an exemplary implementation of a method for analyzing a semiconductor element according to the improved concept.

FIG. 3 shows an image of a top view of a semiconductor element analyzed employing an exemplary implementation of a method for analyzing a semiconductor element according to the improved concept.

FIG. 3 shows a fraction of the back side BS of an actual semiconductor wafer comprising a TSV S5. A circular outline of the TSV S5 is indicated by a dashed white line. Several polymer residues RB are located on the back side BS and appear as white speckles on the black background. In addition, polymer residues RS are located inside the TSV S5 and appear as a white undulated line on the black background.

For generating the image of FIG. 3, the residues RB, RS have been marked using a method for analyzing according to the improved concept, for example as described with respect to FIG. 1, for example using a mixture containing supercritical carbon dioxide and an ATTO 647N dye as the fluorescent substance. Then, the semiconductor element has been illuminated with red visible light with a wavelength matching or approximately matching the absorption wavelength of the fluorescent substance. The nominal absorption wavelength of the ATTO 647N dye is 644 nm.

Due to the illumination, the affixed fluorescent substance was excited and consequently emitted fluorescent light with a wavelength corresponding to the emission wavelength of the fluorescent substance. The emission wavelength of the ATTO 647N dye is 669 nm. The fluorescent light is visible in form of the speckles and the undulated line at the positions of the residues RS, RB. The fluorescent light has been detected with the fluorescence microscope, in particular with a camera, which resulted in the image shown in FIG. 3.

Figure 4:
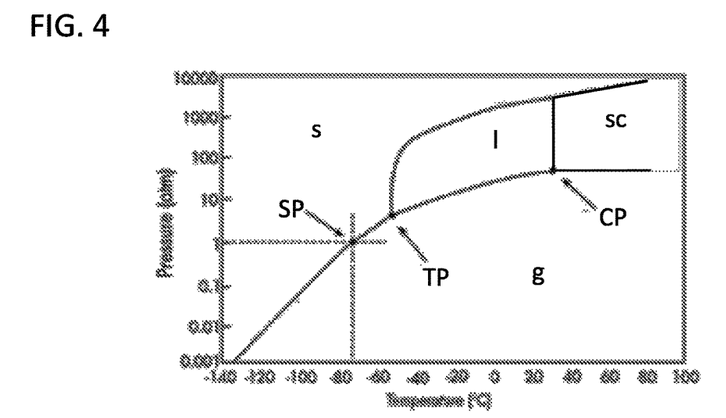
FIG. 4 shows a pressure-temperature phase diagram of carbon dioxide.

FIG. 4 shows a pressure-temperature phase diagram of carbon dioxide. Different parameter ranges, that is ranges for the temperature and the pressure, separated by solid lines are shown that correspond to different phases of carbon dioxide. Therein, temperature is shown in ° C. on the axis of abscissae and pressure is shown in atm on the axis of ordinates. Shown are parameter ranges for which carbon dioxide is in its solid phase s, in its gaseous phase g, in its liquid phase 1 and in its supercritical phase sc. Is highlighted that the solid lines separating the parameter ranges are not necessarily depicted accurately but for providing an overview only. This holds particularly for the lines bordering the supercritical range sc.

In addition, the critical point CP, in particular the liquid-gas critical point CP, and the triple point TP of carbon dioxide are shown. In particular, the critical point is located at a temperature of 30.980 ° C. and a pressure of 72.79 atm. Furthermore, a sublimation point SP at a pressure of 1 atm is shown.

According to a method for analyzing a semiconductor element according to the improved concept, the mixture may be supplied to the pressure chamber for example at a pressure and temperature corresponding to the liquid range 1 of carbon dioxide. Then, the temperature in the pressure chamber is for example increased such that the carbon dioxide and the mixture are transferred beyond the critical temperature into the supercritical range sc. The semiconductor element is then exposed to the mixture in its supercritical phase. Afterwards, the pressure within the pressure chamber may be decreased to reach the gaseous range g of carbon dioxide as explained above.

Alternatively, the mixture may not be transferred to the supercritical phase but for example close to the supercritical range sc. In such implementations of the method, the semiconductor element may be exposed to the mixture in its liquid or gaseous phase.

Figure 5A:
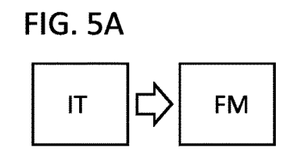
FIG. 5A shows a schematic representation of an exemplary implementation of an arrangement according to the improved concept.

FIG. 5A shows a schematic representation of an exemplary implementation of an arrangement according to the improved concept. The arrangement comprises an impregnation tool IT including the pressure chamber and a fluorescence microscope FM.

Steps of the method for analyzing a semiconductor element according to the improved concept may be carried out using the impregnation tool IT, including the marking of at least the fraction of residues. For further details it is referred to FIGS. 6A and 6B. Other steps of the method for analyzing a semiconductor element according to the improved concept may be carried out with the fluorescence microscope FM, including detecting the marked residues by visualizing the marked residues. The fluorescence microscope FM may for example be implemented in an upgraded automatic optical inspection, AOI, defect tool. A conventional fluorescence microscope FM may be used.

Figure 5B:
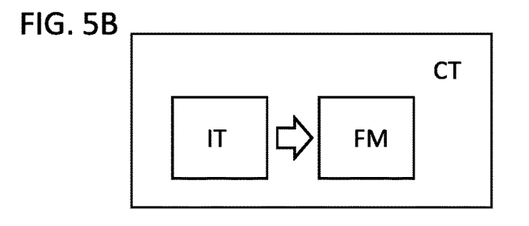
FIG. 5B shows a schematic representation of a further exemplary implementation of an arrangement according to the improved concept.

FIG. 5B shows a schematic representation of a further exemplary implementation of an arrangement according to the improved concept. In the implementation of FIG. 5B, the impregnation tool IT including the pressure chamber and the fluorescence microscope FM are both comprised by a single cluster tool CT. In particular, the fluorescence microscope FM is configured to visualize the marked residues while the semiconductor element is located inside the pressure chamber of the impregnation tool IT.

Figure 6A:
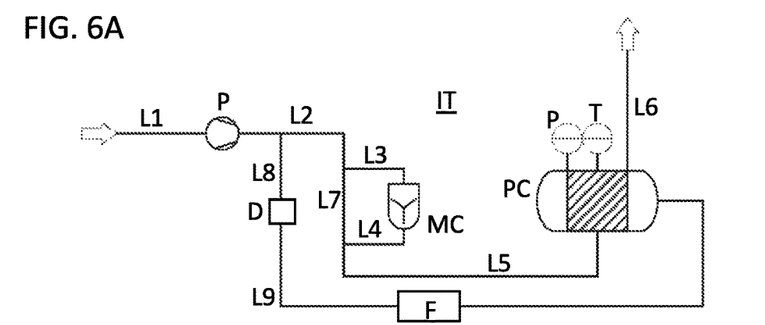
FIG. 6A shows a further exemplary implementation of an arrangement according to the improved concept.

FIG. 6A shows a further exemplary implementation of an arrangement according to the improved concept.

The arrangement comprises an impregnation tool IT and a fluorescence microscope (not shown). The fluorescence microscope is either implemented together with the impregnation tool IT in a single cluster tool as in FIG. 5B or as a separate tool as in FIG. 5A.

The impregnation tool IT comprises a pressure chamber PC, a mixing chamber MC and a pump P, in particular a high-pressure pump, for example implemented as a plunger pump or a piston pump. An input of the pump P may be connected to a carbon dioxide reservoir (not shown) via a first line L1. The carbon dioxide reservoir contains for example liquid carbon dioxide. An input of the mixing chamber MC is connected to an output of the pump P via a second line L2 and a third line L3. An output of the mixing chamber MC is connected to an input of the pressure chamber PC via a fourth line L4 and a fifth line L5. An output of the pressure chamber PC is connected to a gas exhaust (not shown) via a sixth line L6.

The pressure chamber PC is for example constructed of materials comprising stainless steel and/or high-pressure glass in order to avoid a cross contamination of the semiconductor element SE.

The impregnation tool further comprises a control unit comprising a temperature control unit T and a pressure control unit P. The temperature control unit T is configured to control a temperature inside the pressure chamber PC and the pressure control unit is configured to control a pressure inside the pressure chamber PC.

FIG. 6A also shows an optional bypass line L7 bypassing the third line L3, the mixing chamber MC and the fourth line L4. To this end, the integration tool IT may comprise corresponding bypass valves (not shown). In case the impregnation tool IT does not comprise the bypass line L7, the second and the third line L2, L3 may be implemented as a single line and the fourth line and the fifth line L4, L5 may also be implemented as a single line.

Furthermore, an optional flowmeter F and an optional expansion valve D are shown. The expansion valve D is connected to the second line L2 via an eighth line L8 and to a further input of the pressure chamber PC via a ninth line L9. The flowmeter F is arranged to measure a flow through the ninth line L9.

The semiconductor element is for example placed inside the pressure chamber PC.

The liquid carbon dioxide is supplied from the carbon dioxide reservoir to the impregnation tool IT. To this end, the pump P pumps the liquid carbon dioxide to the second line L2. The liquid carbon dioxide is then pumped to the mixing chamber MC. The mixing chamber MC may contain the fluorescent substance for example dissolved in an additional solvent such as dimethyl sulfoxide, isopropyl alcohol or water. Then, the liquid carbon dioxide and the fluorescent substance are mixed in the mixing chamber MC to generate the mixture. The mixture containing the liquid carbon dioxide and the fluorescent substance is then supplied to the pressure chamber PC via the fifth line L5. To this end, an intake valve (not shown) comprised by the arrangement may be controlled by the control unit to supply the mixture to the pressure chamber PC.

Then, the semiconductor element placed inside the pressure chamber PC is exposed to the mixture until the fluorescent substance is affixed to at least the fraction of the residues as described for example with respect to FIGS. 1 to 4. To this end, the temperature and/or the pressure inside the chamber may be increased by using the temperature control unit T and/or the pressure control unit P. In this way, the mixture inside the pressure chamber PC may for example be transferred to its supercritical phase or close to its supercritical phase for the exposure of the semiconductor element to the mixture.

After the residues have been marked by a fixing the fluorescent substance to the residues, a pressure and/or a temperature within the chamber may be decreased by employing the pressure and temperature control units P, T such that the carbon dioxide of the mixture within the pressure chamber PC is transferred to its gaseous phase. The gaseous carbon dioxide may then be pumped down via the exhaust and the sixth line L6.

Then, the marked residues may be detected with the fluorescence microscope as described above.

Via the optional eighth and ninth lines L8, L9 and the expansion valve D, the pressure chamber PC may be flushed with gaseous carbon dioxide prior to and/or after exposing the semiconductor element to the mixture and/or prior to placing the semiconductor element in the pressure chamber PC. To this end, the liquid carbon dioxide that is supplied by the pump P to the eighth line L8 is expanded employing the expansion valve D and consequently supplied as gaseous carbon dioxide to the ninth line L9 and the pressure chamber PC.

It is highlighted that for the sake of clearness, valves comprised by the impregnation tool IT that may be necessary for directing a carbon dioxide flow through the various lines are not shown in FIG. 6A. However, their arrangement becomes an immediately clear to the skilled reader from the purpose and function of the impregnation tool IT and the arrangement of the lines L1 to L9.

Figure 6B:
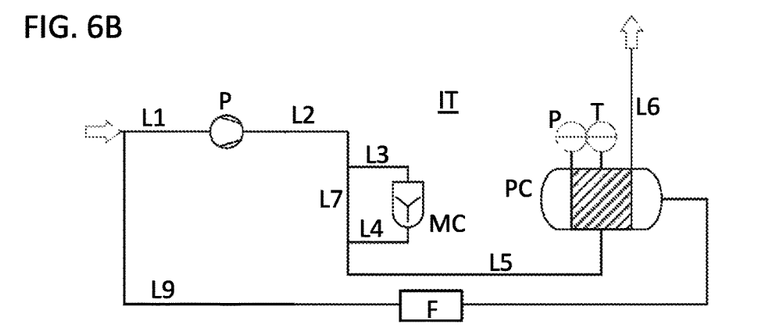
FIG. 6B shows a further exemplary implementation of an arrangement according to the improved concept.

FIG. 6B shows a further exemplary implementation of an arrangement according to the improved concept based on the implementation of FIG. 6A.

In contrast to the implementation of FIG. 6A, the arrangement of FIG. 6B does not comprise the expansion valve D and does not comprise the eighth line L8. Instead, the ninth line L9 connects the pressure chamber PC to the carbon dioxide reservoir. The carbon dioxide reservoir is in the implementation of FIG. 6A adapted to supply liquid carbon dioxide to the first line and to supply gaseous carbon dioxide to the eighth line.

Apart from these differences, the operation of the arrangement of FIG. 6B corresponds to the operation of the arrangement of FIG. 6A.

By employing the improved concept, a semiconductor element may be analyzed with respect to polymer residues non-destructively and with improved efficiency. The improved concept allows for analyzing not only local structural elements such as TSVs, trenches and cavities, but also the whole wafer surface non-destructively. Therefore, mapping of residue distribution as well as statistical analysis of the results for cleaning optimization a process monitoring is possible.

The improved concept may for example be applied if the semiconductor element, in particular the semiconductor substrate, does not show an intrinsic fluorescence in a same wavelength range as the used fluorescent substance.

In particular, semiconductor elements with surface structures such as TSVs with large aspect ratios may be analyzed with a method according to the improved concept. This is particularly advantageous since for large aspect ratios also polymer removal becomes more difficult increasing the importance of an efficient and non-destructive analysis.

However, also semiconductor elements with only a relatively small amount of polymer residues and a random distribution thereof may be efficiently analyzed according to the improved concept, which may be particularly advantageous if improved methods for polymer removal are available.

The invention claimed is:

1. A method for analyzing a semiconductor element comprising polymer residues located on a surface, the method comprising
    marking at least a fraction of the residues by exposing the semiconductor element to a fluorescent substance, wherein the exposing comprises exposing the semiconductor element to a mixture containing the fluorescent substance and carbon dioxide; and detecting the marked residues by visualizing the marked residues on the surface of the semiconductor element using fluorescence microscopy.

2. The method according to claim 1, wherein for the marking the semiconductor element is exposed to the fluorescent substance until the fluorescent substance is affixed or attached to at least the fraction of the residues.

3. The method according to claim 1, wherein the mixture contains the carbon dioxide in its liquid phase.

4. The method according to claim 1, wherein the mixture contains the carbon dioxide in its supercritical phase.

5. The method according to claim 1, further comprising placing the semiconductor element in a pressure chamber; and supplying the mixture to the pressure chamber or supplying the carbon dioxide and the fluorescent substance to the pressure chamber.

6. The method according to claim 5, further comprising transferring the mixture to its liquid phase or to its supercritical phase.

7. The method according to claim 6, comprising increasing a pressure and/or a temperature inside the pressure chamber for the transferring.

8. The method according to claim 2, wherein the visualizing the marked residues using fluorescence microscopy comprises
illuminating at least a part of the semiconductor element with electromagnetic radiation;
detecting fluorescent electromagnetic radiation being emitted by the affixed or attached fluorescent substance as a response to the illumination.

9. The method according to claim 8, wherein the illuminating of the at least a part of the semiconductor element and the detection of the fluorescent electromagnetic radiation are repeated for different focus levels and the method further comprises merging images corresponding to the different focus levels.

10. The method according to claim 9, wherein the different focus levels correspond to different depths of a surface structure or a through-semiconductor-via.

11. The method according to claim 9 further comprising generating a three-dimensional fluorescence image of the illuminated part of the semiconductor element by the merging.

12. The method according to claim 1, wherein the semiconductor element comprises at least one surface structure and the residues located on the surface of the semiconductor element are located on a surface of the at least one surface structure.

13. The method according to claim 12, wherein the at least one surface structure comprises at least one of the following: a through-semiconductor-via, TSV, a trench, a cavity.

14. The method according to claim 12, wherein the at least one surface structure comprises a TSV and the residues are located on a sidewall and/or a bottom wall of the TSV.

15. The method according to claim 1, wherein the semiconductor element is a semiconductor wafer or a semiconductor die.

16. The method according to claim 1, wherein the residues comprise a fluoropolymer and/or an acrylic polymer.

17. A method for manufacturing a semiconductor component comprising
processing a surface of a semiconductor element, wherein a polymer material is utilized or generated;
analyzing the semiconductor element comprising polymer residues originating from the polymer material by employing a method according to claim 1.

18. The method according to claim 17, wherein
the step of processing the surface of the semiconductor element comprises generating a surface structure or a TSV using a deep-reactive ion etching, DRIE, process;
the DRIE process comprises depositing a polymer layer as a passivation layer for preventing from lateral etching; and
the polymer residues located on the surface of the semiconductor element origin at least partially from the polymer layer or from the polymer layer being incompletely removed.

19. The method according to claim 18, wherein the polymer layer comprises a fluoropolymer and/or an acrylic polymer.

20. The method according to claim 18, further comprising a cleaning step to remove the polymer layer, wherein the polymer residues remain on a surface of the surface due to an incomplete removal by the cleaning step.

21. The method according to claim 17, wherein
the step of processing the surface of the semiconductor element comprises a layer deposition process or a layer structuring process;
the polymer residues located on the surface of the semiconductor element are generated at least partially during the layer deposition process or the layer structuring process.

* * * * *